United States Patent
Haumann et al.

(12) 
(10) Patent No.: US 6,285,742 B1
(45) Date of Patent: Sep. 4, 2001

(54) MEDICAL WORKSTATION WITH UNIFIED REMOTE CONTROL OF MULTIPLE COMPONENTS

(75) Inventors: Hans-Juergen Haumann, Erlangen; Franz Meissner, Bamberg, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/245,868

(22) Filed: Feb. 8, 1999

(30) Foreign Application Priority Data

Feb. 11, 1998 (DE) .............................................. 198 05 522

(51) Int. Cl.$^7$ ...................................................... A61B 6/00
(52) U.S. Cl. .............................. 378/116; 378/91; 378/114; 606/2.5
(58) Field of Search .................................. 378/4, 91, 114, 378/116; 606/2.5

(56) References Cited

U.S. PATENT DOCUMENTS

| | | | |
|---|---|---|---|
| 4,184,510 | * | 1/1980 | Murry et al. ..................... 137/565.23 |
| 5,450,079 | * | 9/1995 | Dunaway ................................ 341/23 |
| 5,488,951 | | 2/1996 | Bauer et al. ....................... 128/653.1 |
| 5,528,264 | * | 6/1996 | Kautzer et al. ....................... 345/158 |
| 5,555,120 | * | 9/1996 | Telymonde et al. ................. 378/115 |
| 5,572,567 | * | 11/1996 | Khutoryansky et al. ............ 378/197 |
| 5,734,694 | * | 3/1998 | Khutoryansky et al. ............ 378/197 |
| 6,007,243 | * | 12/1999 | Ergun et al. .......................... 378/197 |
| 6,017,307 | * | 1/2000 | Raines .................................... 600/300 |
| 6,018,565 | * | 1/2000 | Ergun et al. ............................. 378/95 |
| 6,078,947 | * | 6/2000 | Kagermeier .......................... 709/203 |

* cited by examiner

*Primary Examiner*—Drew Dunn
(74) *Attorney, Agent, or Firm*—Schiff Hardin & Waite

(57) ABSTRACT

Medical workstation has at least two separately constructed medical devices that can be operated separately and independently of one another, of which at least one is provided with a remote control. By means of the remote control of the one medical device it is possible to trigger functions of the other medical device or devices.

12 Claims, 3 Drawing Sheets

MEDICAL WORKSTATION WITH UNIFIED REMOTE CONTROL OF MULTIPLE COMPONENTS

BACKGROUND OF THE INVENTION

1. Field of the Invention

The present invention relates to a medical workstation of the type having at least two separately constructed medical devices that can be operated separately and independently of one another, of which at least one is provided with a remote control.

2. Description of the Prior Art

A medical workstation of this sort can include, for example, a patient positioning table, a lithotripter, and a C-arm X-ray device, and serves for the treatment of patients suffering from calculi, e.g. renal calculi, for pain therapy or for osteorestoration. The conventional individual devices which together form the medical workstation generally can be operated completely independently of one another, and are constructed separately, i.e. each of the devices has for example a separate housing or a separate equipment cart, a separate control unit and further means for operating the device. In some circumstances, in the formation of a workstation the individual devices can be coupled mechanically with one another at least partially, as described in European Application 0 606 548 for a lithotripter and a C-arm X-ray device.

All the devices of the workstation, or individual ones, e.g. the patient positioning table, can be equipped with a remote control, permitting an operator to carry out adjustments, e.g. vertical or horizontal movements, of the patient positioning table, without spending time directly at the patient positioning table. The remote control of a device can, for example, be constructed in hard-wired fashion, i.e. it can be connected with the device via a cable, or can operate on the basis of electromagnetic waves.

In the case of a workstation having several devices provided with remote controls, it is a disadvantage that the handling of the multiplicity of remote controls is organizationally and technologically difficult, and thus not very practicable, for an operator. If a medical workstation of the type described above has only one or two medical devices with a remote control, the handling is indeed practicable for an operator, but the execution of the handling of a patient, i.e. the work at the workstation by means of the remote controls, is not very convenient, since in such a case only those medical devices that are provided with a remote control can be remotely operated.

SUMMARY OF THE INVENTION

An object of the present invention is to provide a medical workstation of the general type described above wherein working at the workstation using a remote control is convenient and practicable.

According to the invention, this object is achieved in a medical workstation having at least two separately constructed medical devices that can be operated separately and independently of one another, of which at least one is provided with a remote control, and wherein by means of the remote control of the at least one medical device provided with a remote control, functions of the other medical device can be triggered. In the inventive medical workstation one, and preferably only one, medical device of the workstation is provided with a remote control, and by means of remotely controlling this one medical device, it is possible to remotely operate and control not only the that medical device but also the other medical devices that together with the directly remotely controlled medical device form a workstation. For this purpose, according to a version of the invention the remote control of the one medical device includes control means for triggering functions of the other medical devices of the workstation. In this way, it is achieved according to the invention that the remotecontrolled operation of several medical devices is not only practicable but also is convenient, since the remote control of only one device of the workstation enables the operation of several medical devices.

Within the scope of the invention, however, several medical devices also can be provided with a direct remote control, with each remote control of a device preferably including operating functions for triggering functions of other medical devices of the workstation. In this way, the treatment of a patient at the workstation can take place at least in part with a single remote control that is allocated to one of the medical devices.

In a particularly preferred embodiment of the invention the medical devices are connected electrically with one another. In the case of a remote control that operates on the basis of electromagnetic waves (e.g. RF, light, etc.), it is thus necessary, in an economically advantageous manner, only for the one medical device provided with the remote control to have a suitable receiver for the electromagnetic waves, since the further signal transmission to the respective destination device of the workstation can take place in hard-wired fashion.

In an embodiment of the invention the remote control unit has a display capable of displaying graphics, so that the display can represent not only (as has previously been standard) alphanumeric characters and abbreviations, but can also display large-format graphic characters and symbols. In this way, the user convenience of such a remote control is further increased, since alphanumeric characters and abbreviations can be provided with graphic symbols that contribute to the better understanding of the alphanumeric characters, in particular of the abbreviations. In addition, with respect to user convenience, such a remote control facilitates operation by doctors working at such medical workstations who have been trained to recognize such graphics quickly. In the most advantageous case, it is even possible to do entirely without alphanumeric characters, insofar as the graphic characters and symbols that can be displayed on the graphics-capable display means are self-explanatory. A "graphics-capable display" means a display with pixels wherein the pixels are at least partially individually addressable electrically, so that in addition to alphanumeric characters it is also possible to represent graphic characters and symbols on the display.

In a further version of the invention the remote control is provided with an electrical connecting line to which a medical device is connected. In this way, it is also possible to control or trigger functions of a medical device for which safety is critical, e.g., in the case of an X-ray device, the triggering of X-ray exposures, using the remote control. In comparison to a remote control that operates on the basis of electromagnetic waves, such a hard-wired remote control offers the advantage that disturbing signals that may be present in rooms in which the medical device is used cannot lead to an unwanted triggering of critical functions that can have adverse effects on the health of a patient.

According to an embodiment of the invention, the remote control is connected in detachable fashion to an interface of the one medical device. In this way, the remote control can easily be separated from the medical device in the case of non-use, so that the connection cable of the remote control to the medical device does not have a disturbing effect, e.g. given displacement movements of the device.

In a particularly preferred embodiment of the invention various operating menus with operating functions can be represented on the graphics-capable display of the remote control, and the remote control includes operating elements for selecting the operating menus and/or the operating functions. Supplementary to the representation of large-format graphic characters and symbols on the graphics-capable display, the remote control thus enables a menu-controlled operation of the medical device, which leads to a still more convenient operation of the medical device.

In another version of the invention the medical workstation includes a lithotripter and at least one of an X-ray device or a patient positioning table. The lithotripter is provided with a remote control, and the remote control of the lithotripter includes operating means for triggering focused acoustic waves of the source of focused acoustic waves of the lithotripter, for triggering movements of a displaceable patient positioning table, and for adjustments and for triggering and storage of X-ray exposures of an X-ray device. Thus, if a medical workstation is fashioned from a lithotripter provided with a remote control, a patient positioning table that can be displaced horizontally and vertically, and an X-ray device, by connecting them with one another electrically, then with the remote control of the lithotripter it is possible e.g. not only to trigger focused acoustic waves of the lithotripter, but also to displace the patient positioning table, e.g. vertically and/or horizontally, to carry out adjustments to the X-ray device, to trigger X-ray exposures of the X-ray device, or to store obtained X-ray exposures. The operating convenience of a medical workstation comprising at least one medical device provided with a remote control constructed in this way is significantly increased.

DESCRIPTION OF THE PREFERRED EMBODIMENTS

Figure 1:
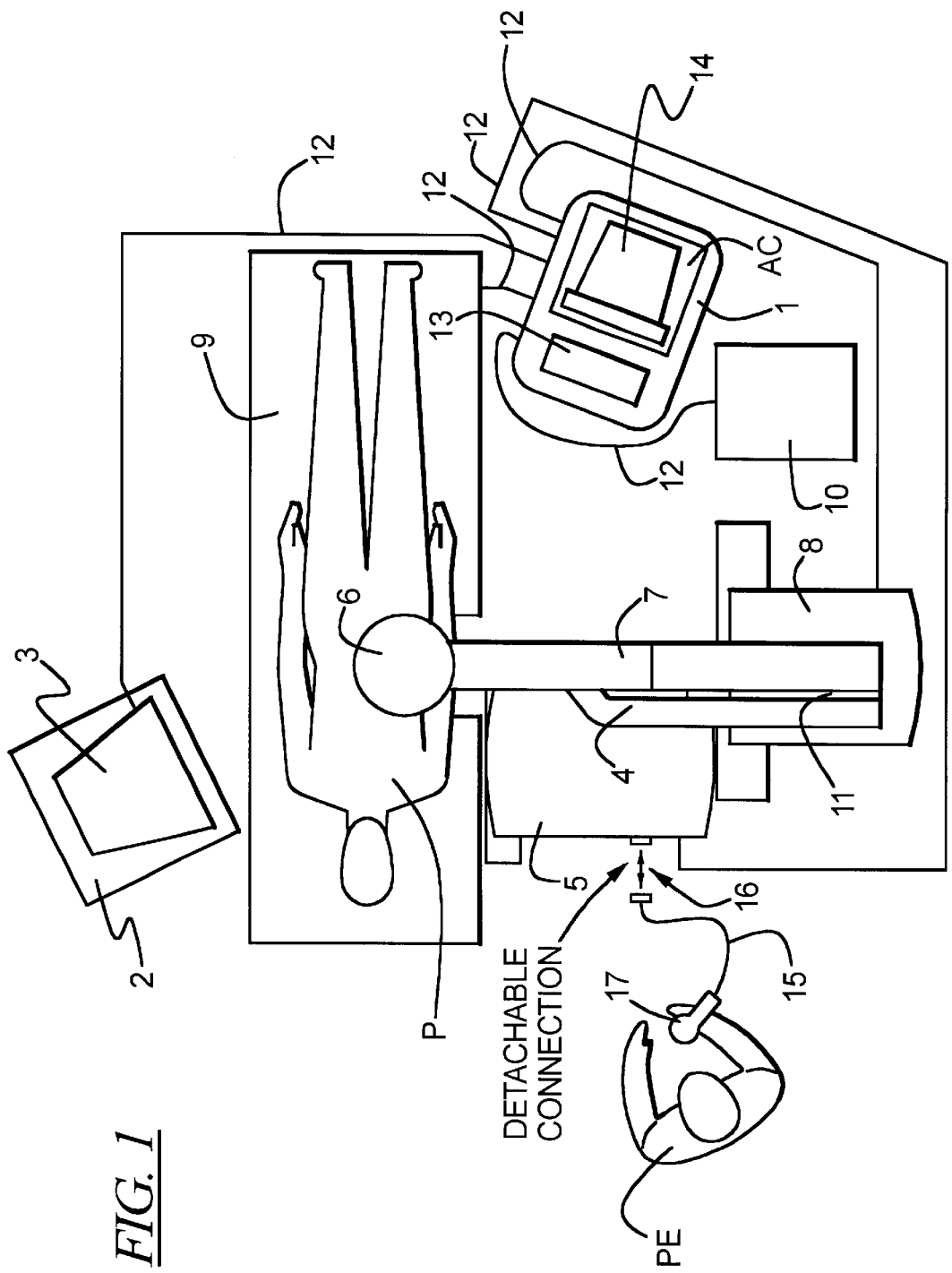
FIG. 1 is a view from above of an inventive medical workstation in the form of a workstation for lithotripsy.
Figure 2:
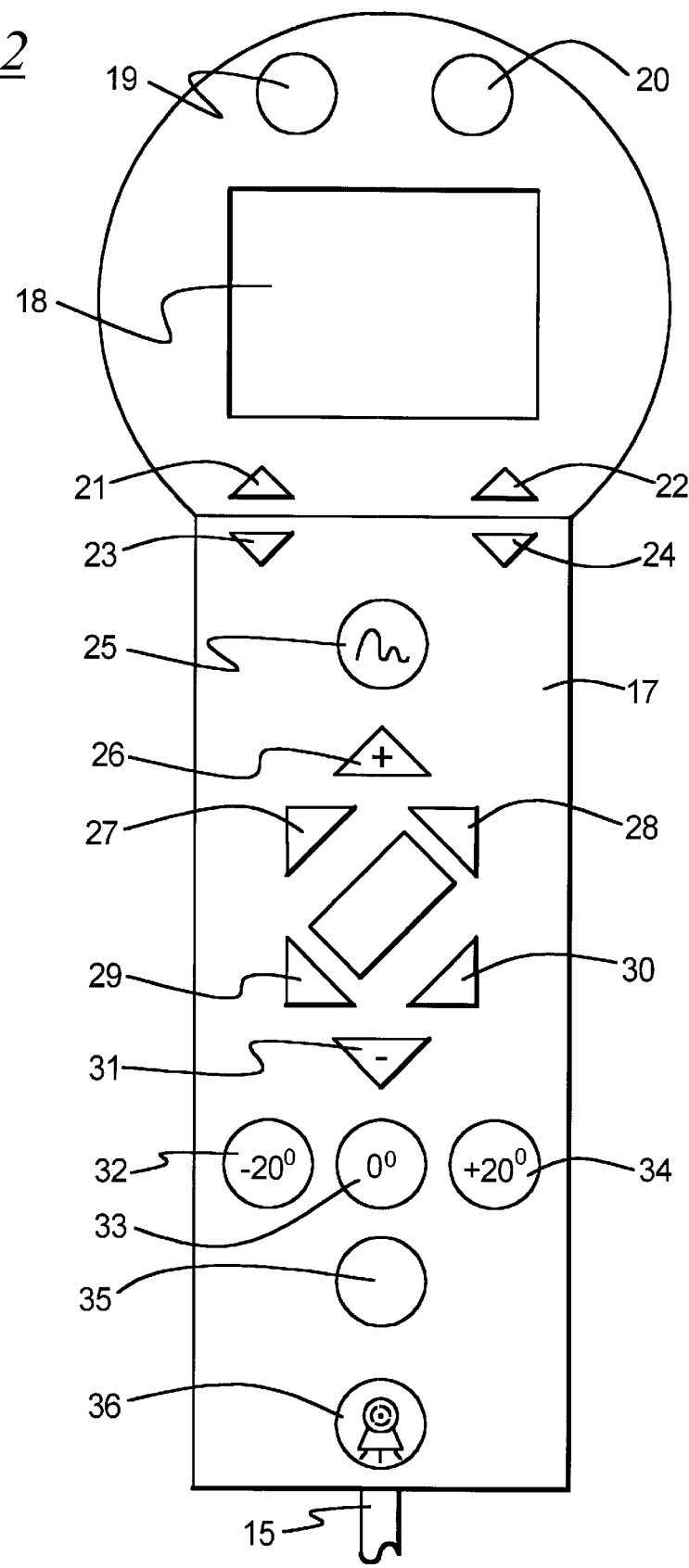
FIG. 2 shows an embodiment of a remote control for a medical device of the workstation shown in FIG. 1.

FIG. 1 shows a top view of an inventive medical workstation. The medical workstation includes various medical devices that are constructed separately and can be operated independently of one another, and serves in the case of the present embodiment for the treatment of a patient P suffering from calculi, e.g. renal calculi. The known individual medical devices of the medical workstation include a lithotripter 5 having a source (not shown) of focused acoustic waves, arranged on a mount arm 4, for disintegrating calculi, a C-arm X-ray device 8 with a C-arm 7 provided with an X-ray source (not shown) and an X-ray receiver 6, a patient positioning table 9 that can be displaced vertically and horizontally, and a diagnostic ultrasound device 10 with an ultrasound head (not shown). The known medical devices 5, 8, 9, 10 (not described in more detail) can be operated independently of one another. The devices 5, 8, 9, 10 each have, in a way not shown in more detail, a separate housing or a separate equipment cart, separate controllers and circuits for their operation.

In the present embodiment, the mount arm 4 of the source of focused acoustic waves of the lithotripter 5 and the C-arm X-ray device 8 are coupled with one another in mechanically detachable fashion via a mechanism 11 (not shown in more detail) in such a way that the focus of the source (not shown) of focused acoustic waves of the lithotripter 5 is located approximately in the beam path of the central beam of an X-ray beam bundle that proceeds from the X-ray source (not shown) to the X-ray receiver 6 of the C-arm X-ray device 8.

The C-arm X-ray device 8 and the diagnostic ultrasound device 10 of the medical workstation serve, in a known way, for the location of the renal calculi (not shown in FIG. 1) that are to be disintegrated in the body of the patient P. The source of focused acoustic waves of the lithotripter 5 has, in a known way, a central region into which the ultrasound head of the diagnostic ultrasound device 10 can be introduced for location purposes.

The patient positioning table 9 and the C-arm X-ray device 8 coupled with the lithotripter 5 can be displaced relative to one another in a known way for the location of the renal calculi and for the adjustment of the focus position of the source of focused acoustic waves of the lithotripter 5 on the renal calculi of the patient P.

For the location of the renal calculi in the body of the patient P using the C-arm X-ray device 8 and/or the diagnostic ultrasound device 10, in order to orient the focus of the source of focused acoustic waves of the lithotripter 5 on the renal calculi of the patient P and for the treatment of the patient P with focused acoustic waves, it is necessary that the lithotripter 5, the C-arm X-ray device 8, the diagnostic ultrasound device 10 and the patient positioning table 9 exchange a certain amount of data with one another. For this purpose, the medical devices 5, 8 and 9 and 10, as well as a monitor 3 arranged on a cart 2, are detachably connected to a terminal unit 1 of the medical workstation. The monitor 3 is provided for the central display of information obtained using the medical devices. The connection of the medical devices 5, 8, 9, 10 and of the monitor 3 to the terminal unit 1 take place respectively via a system line 12, which is routed from the medical devices 5, 8, 9, 10 and the monitor 3 to the terminal unit 1. A system line 12 of one of the medical devices 5, 8, 9, 10 or of the monitor 3 contains, in a way not shown, several connecting cables, combined in the system line 12, for the transmission of control data, the transmission of image data and for the transmission of energy. The connection of the system line 12 of a device to the terminal unit 1 takes place via a system plug. The terminal unit 1 is provided with corresponding receptacles (not shown) for receiving the system plugs of the system lines 12 of the medical devices 5, 8, 9, 10 and of the monitor 3.

The terminal unit 1 has a control computer in the form of a personal computer PC, which is connected via a communication bus (not shown) with the receptacles of the terminal unit 1. The terminals of the receptacles for the connecting cables for data and image data transmission of the system lines 12 or of the system plugs, are routed to the communication bus of the terminal unit 1. The terminals of the receptacles for the connecting cable for energy transmission of the system lines 12 or of the system plugs are routed to an energy supply unit (not shown) of the terminal unit 1, which supplies all devices 5, 8, 9, 10 and the monitor 3 of the medical workstation with electrical energy via the system lines 12.

The PC of the terminal unit 1 controls, via the communication bus and the system lines 12, the data exchange between the medical devices 5, 8, 9, 10 during the treatment process of the patient P. The PC also controls the data exchange of image and document data between the PC and the medical devices 5, 8, 9, 10, as well as the display of the items of information obtained by means of the medical devices 5, 8, 9, 10 on the monitor 3 connected to the PC of the terminal unit 1. The information can for example be image information obtained by means of the C-arm X-ray device 8 or by means of the diagnostic ultrasound device 10, or, if necessary, can for example be items of status and position information of the medical devices 5, 8, 9, 10. The display of the information can take place successively or simultaneously, whereby the latter can be achieved by division of the display screen of the monitor 3 into different, possibly variable, regions.

In addition, the PC of the terminal unit 1 includes means for documentation, namely electronic storage media, e.g. a hard disk or known drives for magnetic storage units, and input and output modules in the form of a keyboard 13, a monitor 14 and a printer (not shown). In this way, in the case of the present medical workstation, for the displaying of items of information obtained using the medical devices 5, 8, 9, 10, e.g. items of image information of the C-arm X-ray device 8, on the monitor 3, on the monitor 14 of the terminal unit 1 it is simultaneously possible to display, input, update, and store e.g. patient and/or treatment data, or findings can be printed out using the printer. It is also possible to save items of information obtained by means of the medical devices 5, 8, 9, 10, e.g. on a magnetic storage unit, or to print them out on the printer.

In the case of the present embodiment, the lithotripter 5 has a remote control 17 connected in detachable fashion to an interface 16 of the lithotripter 5 using a connection line 15. The remote control 17 of the lithotripter 5 is provided not only for the operation of the lithotripter 5 itself, but also for controlling at least some of the operation of medical devices 8, 9 connected electrically with the lithotripter 5 via the system lines 12 and the terminal unit 1.

The remote control 17 has operating elements for the lithotripter 5 and a graphics-capable display 18, on which there can be represented both alphanumeric and large-format graphic characters, symbols and operating menus, with operating functions for simplified and improved operation or, respectively, operator interface using the remote control 17. The remote control 17 also includes operating elements for the medical devices 8 and 9 connected electrically with the lithotripter 5. In the present embodiment, the remote control 17 has keys 19, 20 for menu mode, keys 21 to 24 for parameter adjustment of the lithotripter 5, a key 25 for triggering focused acoustic waves of the source of focused acoustic waves of the lithotripter 5, keys 26 to 31 for controlling vertical and horizontal movements of the patient positioning table 9, keys 32 to 34 for adjusting the angle of the C-arm 7 of the C-arm X-ray device 8 in an angular region of +/- 20° from the zero setting of the C-arm 7 shown in FIG. 1, a key 35 for image storage of a recorded X-ray image, and a key 36 for triggering X-ray radiation of the C-arm X-ray device 8.

The actuation of one of the keys 32 to 34 for the adjustment of the angle of the C-arm 7 of the C-arm X-ray device 8 has, for example, the effect that the C-arm 7 is pivoted relative to the patient P by the corresponding angle, corresponding to the actuated key 32, 33 or 34. The transmission of the corresponding adjustment signal thereby takes place from the remote control 17, via its connecting cable 15 and the interface 16 to the lithotripter 5, via the system line 12 thereof to the terminal unit 1, and from the terminal unit 1 via the system line 12 of the C-arm X-ray device 8 to the C-arm X-ray device 8.

It is thus clear that in the context of the treatment process of a patient P at the medical workstation, functions of the C-arm X-ray device 8 or of the patient positioning table 9 can be triggered without difficulty by means of the electrical connection of the medical devices 5, 8, 9, 10 of the workstation with one another, using the remote control 17 of the lithotripter 5.

Figure 3:
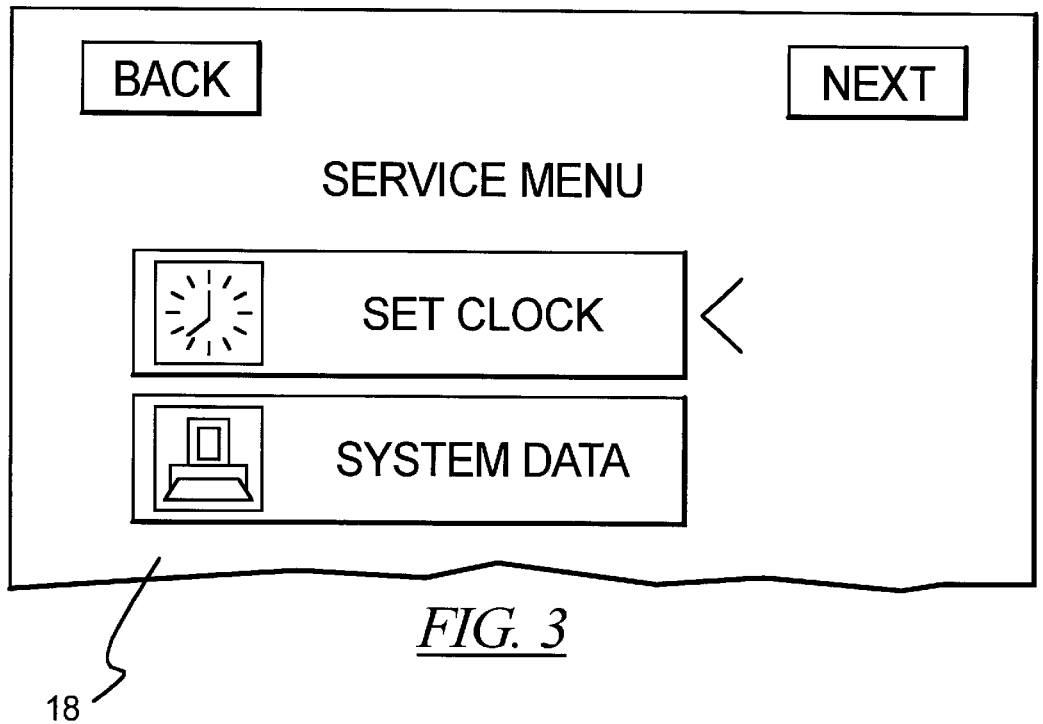
FIG. 3 and FIG. 4 respectively show operating menus that can be displayed on the graphics-capable display of the remote control of FIG. 2.
Figure 4:
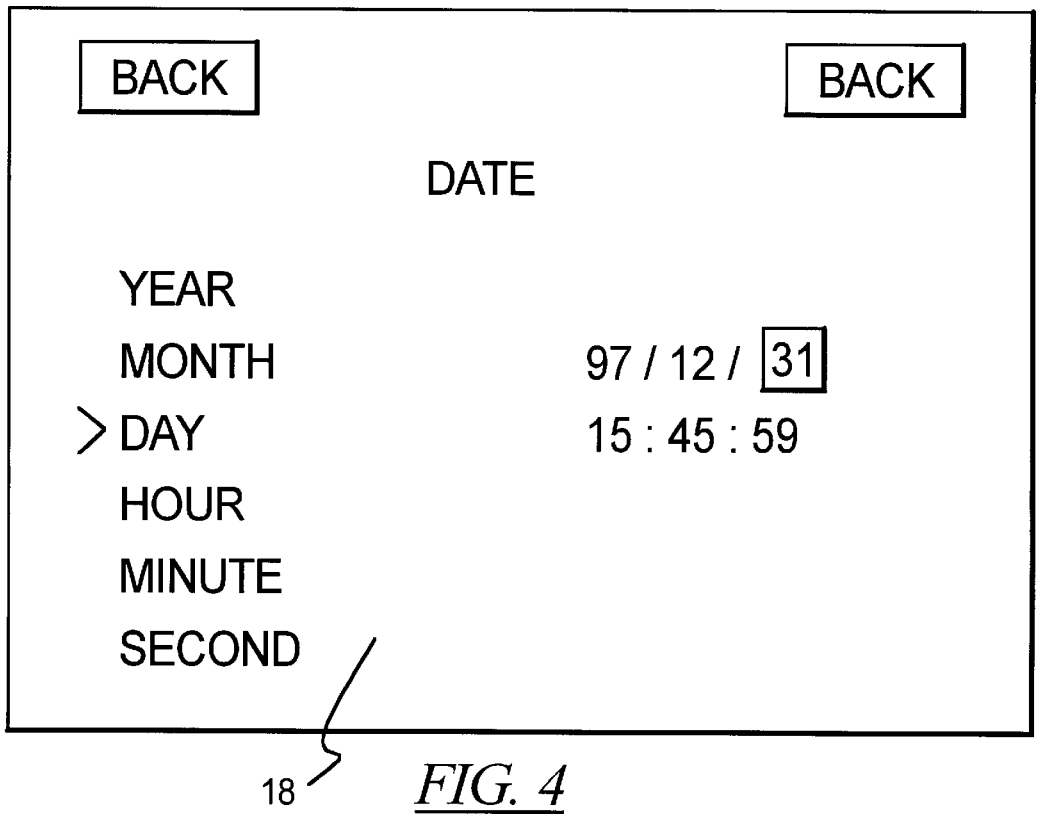

FIG. 3 shows a segment of an operating menu of the remote control 17 that can be displayed on the graphic display 18 of the remote control 17, in the form of a service menu of the lithotripter 5. The service menu contains operating functions in the form of so-called buttons, e.g. the button "back." If for example, using one of the keys 19, 20 for menu guidance, the menu point "set clock" is selected, a branching takes place to a submenu shown in FIG. 4, in which the system time and the date can be adjusted using the keys 21 to 24 for parameter adjustment of the remote control 17.

A further submenu presented as an example is the submenu "system data"; when it is called, system data of the lithotripter 5 can be retrieved or can be adjusted via the keys 21 to 24 of the remote control 17.

The selectable operating functions and/or sub-menus are provided at least partially with graphic symbols in order further to increase the clarity of the selectable operating functions and/or sub-menus. The graphic symbols and characters thereby need not necessarily, as shown in FIG. 3, occur in combination with alphanumeric text, but rather, insofar as they are self-explanatory, can stand alone without corresponding accompanying text.

It is thus clear that with a graphic display means of a remote control the operation of the remote control can be organized in a more convenient and simplified manner for an operator PE, by adding graphic characters, alphanumeric texts and/or abbreviations for better understanding, by providing, in the case of menu-controlled operation, selectable operating functions and/or sub-menus with graphic characters for better clarity, or by completely replacing corresponding operating functions and/or submenus with self-explanatory graphic characters.

The inventive medical workstation has been described above for the example of a workstation for lithotripsy. However, the workstation can be used not only for disintegrating calculi, but also for pain therapy or for osteorestoration. Moreover, the inventive medical workstation can also be a different medical workstation, e.g. an endourological one, or can be a workstation for prostate therapy.

If necessary, a hard-wired remote control need not necessarily be connected detachably to a medical device, e.g. the lithotripter; rather, it can be connected fixedly to the medical device.

In addition, it is not necessary that only one medical device be provided with such a remote control; rather, it is also possible for other medical devices to have a remote control constructed with a graphics-capable display means, whereby the remote controls can be provided with corresponding operating means for triggering particular operating functions of other medical devices that can be connected to the medical device.

The medical devices thereby need not necessarily be connected via a terminal unit 1, but also can be connected directly with one another for data exchange.

The construction of the remote control 17 is to be understood only as an example. The remote control 17 can be constructed differently as to its size, shape and in relation to the operating elements; e.g., the remote control can also have additional operating elements for the operation of the ultrasound device 10.

The remote control need not necessarily be a hard-wired remote control; it can alternatively operate, for example, on the basis of electromagnetic waves, insofar as the remote control is not provided for the triggering of functions of a medical device for which safety is critical, for example for the triggering of X-ray exposures.

If in such a case the medical devices are not connected with one another electrically, each of the medical devices that is to be operated remotely, for example by means of a remote control of the lithotripter that operates on the basis of electromagnetic waves, must be provided with a suitable receiver for the electromagnetic waves emitted by a transmitter of the remote control.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical workstation comprising:
    at least two separate, different and independently operable medical devices respectively for performing different medical procedures when independently operated;
    a first of said medical devices having remote control means for remotely controlling said first of said medical devices to perform a first of said different medical procedures; and
    said remote control means also including means for triggering at least one function of a second of said medical devices in a second of said different medical procedures while said first of said medical devices is performing said first of said different medical procedures.

2. A medical workstation as claimed in claim 1 wherein said remote control means comprises a hand-held remote control unit, and wherein said means for triggering functions of said second of said medical devices comprises operating elements on said remote control unit for triggering said functions of said second of said medical devices.

3. A medical workstation as claimed in claim 1 wherein said means for triggering said functions of said second of said medical devices comprises an electrical connection between said first of said medical devices and said second of said medical devices for relaying a signal, emitted by said remote control means to said first of said medical devices, to said second of said medical devices.

4. A medical workstation as claimed in claim 1 wherein said remote control means comprises a graphics-capable display.

5. A medical workstation as claimed in claim 4 wherein said remote control means comprises means for displaying different operating menus with operating functions on said graphics-capable display, and wherein said remote control means comprises operating elements for selecting menu items and operating functions which are displayed on said graphics-capable display.

6. A medical workstation as claimed in claim 1 wherein said remote control means comprises an electrical line connecting said remote control means to said first of said medical devices for transmitting signals from said remote control means to said one of said medical devices.

7. A medical workstation as claimed in claim 6 wherein said one of said medical devices has an interface for said electrical line, and wherein said remote control means is detachably connected to said interface.

8. A medical workstation as claimed in claim 1 wherein said first of said medical devices comprises a lithotripter.

9. A medical workstation as claimed in claim 1 wherein said second of said medical devices comprises a medical device selected from the group consisting of an X-ray device and a patient positioning table.

10. A medical workstation as claimed in claim 1 wherein said first of said medical devices comprises a lithotripter and wherein said second of said medical devices comprises a medical device selected from the group consisting of an X-ray device and a patient positioning table.

11. A medical workstation as claimed in claim 10 wherein said remote control means comprises operating elements for triggering focused acoustic waves from said lithotripter, operating elements for triggering movements of said patient positioning table, and operating elements for storing and triggering X-ray exposures of said X-ray device.

12. A medical workstation as claimed in claim 1 wherein said second of said medical devices performs a plurality of functions in said second of said different medical procedures, and wherein said means for triggering at least one function of said second of said medical devices comprises means for triggering only selected functions in said plurality of functions, said selected functions being less than all of said plurality of functions, to augment operation of said first of said medical devices in performing said first of said different medical procedures.

* * * * *